(12) United States Patent
Higo et al.

(10) Patent No.: US 10,023,552 B2
(45) Date of Patent: Jul. 17, 2018

(54) METHOD OF PREPARING A LIQUIRITIGENIN PRECURSOR

(71) Applicant: Haruo Higo, Osaka (JP)

(72) Inventors: Haruo Higo, Osaka (JP); Toshiya Masuda, Osaka (JP)

( * ) Notice: Subject to any disclaimer, the term of this patent is extended or adjusted under 35 U.S.C. 154(b) by 0 days.

(21) Appl. No.: 15/322,582

(22) PCT Filed: Jul. 1, 2015

(86) PCT No.: PCT/JP2015/069021
§ 371 (c)(1),
(2) Date: Dec. 28, 2016

(87) PCT Pub. No.: WO2016/002848
PCT Pub. Date: Jan. 7, 2016

(65) Prior Publication Data
US 2017/0158661 A1    Jun. 8, 2017

(30) Foreign Application Priority Data

Jul. 2, 2014 (JP) ................. 2014-136494
Dec. 25, 2014 (JP) ................. 2014-262279

(51) Int. Cl.
| C07D 311/48 | (2006.01) |
| C07D 311/42 | (2006.01) |
| C07C 45/41  | (2006.01) |
| C07C 45/64  | (2006.01) |
| A23L 33/105 | (2016.01) |
| A23L 2/52   | (2006.01) |

(52) U.S. Cl.
CPC .............. *C07D 311/42* (2013.01); *A23L 2/52* (2013.01); *A23L 33/105* (2016.08); *C07C 45/41* (2013.01); *C07C 45/64* (2013.01); *A23V 2002/00* (2013.01)

(58) Field of Classification Search
CPC ........ C07D 311/42; C07C 45/41; C07C 45/64
See application file for complete search history.

(56) References Cited

U.S. PATENT DOCUMENTS 5,106,871 A    4/1992 Komazawa et al.

FOREIGN PATENT DOCUMENTS

WO    88/04288 A1    6/1988

OTHER PUBLICATIONS

Chaturvedi, Indian J Chem, 1992, vol. 31B, 340-341.*
Liao, Chem Pharm Bull, 52(10), 1162-1165, 2004.*
Internal Search Report dated Sep. 8, 2015 issued in corresponding International application No. PCT/JP2015/069021.
Chaturvedi, R. et al, "An improved procedure for flavanones", Indian Journal of Chemistry, 1992, vol. 31B, p. 340-341.
Yang, L. et al, "The Synthesis of Liquiritigenin and Isoliquiritigenin", Yaoxue Xuebao, 1994, vol. 29, No. 11, p. 877-880.
Hu et al. European Journal of Medical Chemistry, 2010, 45, p. 3453-3458.

* cited by examiner

*Primary Examiner* — D Margaret M Seaman
(74) *Attorney, Agent, or Firm* — IP Business Solutions, LLC

(57) ABSTRACT

[Problem] To provide a process suitable for mass-producing of iso-liquiritigenin.
[Solution] A process for preparing iso-liquiritigenin, which comprises steps of coupling a 4-alkoxycinnamic acid represented by formula (I) with a 1,3-alkoxybenzene represented by formula (II) through the Friedel-Crafts reaction (A) to synthesize a tri-alkoxy-iso-liquiritigenin represented by formula (III), to crystallize out the reaction product, and eliminating the protecting groups therefrom to obtain iso-liquiritigenin, represented by formula (IV). The iso-liquiritigenin (IV), is administered as a precursor for liquiritigenin represented by formula (V) to the body, thereby obtaining in vivo a pharmacological effect of the (−) isomer of liquiritigenin.

2 Claims, 2 Drawing Sheets a:MOMCl,K₂CO₃/Me₂CO; b:ZnCl₂,AcOH,Reflux; c:4,KOH/EtOH; d:AcONa/EtOH; e:HCl,EtOH,Reflux

METHOD OF PREPARING A LIQUIRITIGENIN PRECURSOR

The present invention relates to a method of preparing iso-liquiritigenin as a precursor of liquiritigenin contained in licorice root.

liquiritigenin, which is generally extracted from licorice roots, has been recognized widely as a good herbal medicine. However, the extraction method of liquiritigenin from licorice roots requires a final purification step by reverse phase chromatography after a thermally extraction step and a removal step of sugars portion (glucose or apiose) after hydrolysis. Therefore, extraction from licorice root makes licorice valuable and a high cost (at a price/g of 10,000 Chinese yuan or more). Moreover, due to difficult cultivation of licorice root the liquiritigenin cost is becoming increasingly high.

Under the situation, there were proposed the following attempts to artificially synthesize liquiritigenin contained in licorice roots. The first method is shown in FIG. 2, wherein p-hydroxy benzaldehyde is used as a starting material, to synthesize 4-carboxy cinnamic acid and add 1,3-dihydroxybenzene thereto to obtain liquiritigenin (Non-Patent Document 1), but it has a disadvantage of low yields. On the other hand, the second method as shown in FIG. 3 is proposed, wherein p-hydroxybenzaldehyde is used as a starting material, and the p-position of hydroxyl group is protected by MOM reagent, while the hydroxyl group of 1,3-dihydroxybenzene is protected by MOM Reagent to add both compound (Non-Patent Document 2). However, in practice, purification step by column chromatography is required in almost all stages (due to the yield and the oil-like product). Moreover, the other additional test experiment proved that the yield of the coupling step was dropping to 42% due to the scale-up, and in the ring-closing reaction from iso-liquiritigenin to liquiritigenin, the starting material (iso-liquiritigenin) and the desired product (liquiritigenin) are in the equilibrium state, whereby the yield does not increase. In addition, it is difficult to separate the raw material and the desired product in the ring-closing stage, so that liquiritigenin becomes tailing under the final chromatographic purification conditions, which causes significantly low rate. Moreover, the carcinogenicity of MOM protecting reagent and the requirement of two extra steps for protection and de-protection make the process not suitable for mass production, although the second method is effective in the laboratory level.

The documents of the prior art
Non-patent literature 1: Pharmaceutical science report Acta Pharmaceutica Sinica 1994, 29 (11): 877~880
Non-patent literature 2: Hu etc. European Journal of Medical Chemistry, 2010, 45, 3453-3458

THE SUMMARY OF THE INVENTION

Problems to be Solved of the Invention

The object of the invention is to provide a method of mass production of liquiritigenin without use of chromatograph, as well as without use of the MOM protecting reagent with carcinogenic property, moreover without use of artificially change process from iso-liquiritigenin to liquiritigenin because of loss of yield caused by the equilibrium reaction as well as existence of (+) and (−) isomers of liquiritigenin, different from natural liquiritigenin.

Means for Solving the Problems

The invention was made on the basis on the foundation that, cultivation of iso-liquiritigenin in an organic acid aqueous solution, typically citric acid makes iso-liquiritigenin naturally converted to liquiritigenin (−) and administration of iso-liquiritigenin cultured in the organic acid is to obtain pharmacological effect of this liquiritigenin (−) in the body. In the present invention, firstly a p-alkoxy cinnamic acid as a starting material, is coupled through Friedel-Crafts reaction with a p-alkoxy benzene to crystalize out a tri-alkoxy-iso-liquiritigenin, which is deprotected to mass-produce iso-liquiritigenin. The iso-liquiritigenin cultured with organic acid can be converted to liquiritigenin (−) and a pharmacological effect of liquiritigenin (−) can be obtained in the body.

The Effect of the Invention

According to the present method, it is possible to obtain a target substance at a high yield by crystallization methods. That is. It is possible to prepare the target substance at a low cost because of no use of gas chromatograph. Further, iso-liquiritigenin can be converted to liquiritigenin (−) in vivo. liquiritigenin made by culturing iso-liquiritigenin in an organic acid aqueous solution including citric acid had better to be used. According to Japanese Patent No. 5,611,394, Liquiritigenin (−) of 10 μg/ml, show inhibitory effects of 96.08% against human liver cancer cells SMMC7721, 73.76% against human poorly differentiated gastric cancer line BGC-823, 64.40% against human for Hayayo grain cell leukemia cells HL-60, and although it is slightly lower, 35.06% against human lung cancer cells A549. These inhibitory effects are higher than the inhibitory effect on cancer cells of adriamycin (as shown in the following Table 2 and Table 3).

TABLE 2

Inhibition rate of (Liquiritigenin) against each cancer cells

| Conc. μg/ml | SMMC7721 Inhibition % | A549 Inhibition % | BGC-823 Inhibition % | HL-60 Inhibition % |
|---|---|---|---|---|
| 1 | 23.17 | 7.76 | 24.41 | 50.95 |
| 10 | 96.08 ++ | 35.66 + | 73.76 ++ | 64.40 ++ |
| 100 | 98.00 | 93.03 | 97.52 | 99.30 |

TABLE 3

Inhibition rate of (adriamycin) against each cancer cells

| Conc. Mol/l | SMMC7721 Inhibition % | A549 Inhibition % | BGC-823 Inhibition % | HL-60 Inhibition % |
|---|---|---|---|---|
| $1 \times 10^{-7}$ | 10.28 | 16.42 | 17.86 | 61.59 |
| $1 \times 10^{-6}$ | 58.40 | 16.42 | 45.80 | 59.73 |
| $1 \times 10^{-5}$ | 97.47 | 90.44 | 97.67 | 99.09 |

Further, according to the cultivation method of the present invention, different from the artificial synthesis, liquiritigenin (+) and (−) form cannot be prepared at the same time. That is, according to the present invention, iso-liquiritigenin can be obtained at a higher yield and can be effectively utilized. Furthermore, according to the cultivation method in the organic acid, typically mainly consisting of citric acid, of the present invention, it is easy to obtain just only liquiritigenin (−) having a high pharmaceutical effect. Accordingly, this inventive method is much better than the conventional artificial synthesis at a point of yield of liquiritigenin (−). That is, according to the present invention, no existence of liquiritigenin (+) form in the final product need the toxicity test.

According to the present invention, as shown in FIG. 1, firstly there is provided with the coupling reaction (A) wherein a p-alkoxy cinnamic acid represented by the formula (I) and a 1,3-di-alkoxy benzene represented by the formula (II) are synthesized to give a tri-alkoxy iso-liquiritigenin represented by the formula (III) and then leave a protective group to obtain iso-liquiritigenin (IV). In the general formula (I), (II), and (III), R may be selected from methyl, ethyl or butyl, so that a methoxy group wherein R is methyl, is usually used. In the reaction, p-alkoxy cinnamic acids of formula (I) is halogenated by adding a halogenating agent and a p-alkoxy benzene represented by the formula (II) is added therein. After that, under a catalyst (metal halide, for example, aluminum chloride, etc.) a tri-alkoxy cinnamic acid represented by the formula (IIIa) can be obtained by e-substitution reaction to the hydrogen of a given aromatic ring. Secondly, in the reaction (B) iso-liquiritigenin of the formula (IV) can be obtained by elimination of the protective group. By the conventional ring-closure reaction (C), iso-liquiritigenin of the formula (IV) is generally converted into liquiritigenin (+) body and (−) body of formula (V), which are necessary to be separated by chiral resolution. Therefore, in order to obtain liquiritigenin (−) derived from licorice, iso-liquiritigenin should be converted to liquiritigenin (−) by using the isomerase enzyme. Instead of this, we also found that liquiritigenin (−) can be obtained by cultivation step in an aqueous solution of an organic acid.

In case of carrying out the present invention, p-methoxy-cinnamate is preferred to be used as p-alkoxy cinnamic acid, but p-ethoxy cinnamic acid and p-butoxy cinnamic acid may be used. In the examples below, tri-methoxy cinnamic acid of the formula (I a) and 1.3-dimethoxy benzene of the formula (II a) are reacted to synthesize tri-methoxy iso-liquiritigenin of the formula (III a), which is converted to iso-liquiritigenin by leaving a protective group.

THE SUMMARY OF THE DRAWINGS

THE EMBODIMENT OF CARRYING OUT THE INVENTION

Figure 1:
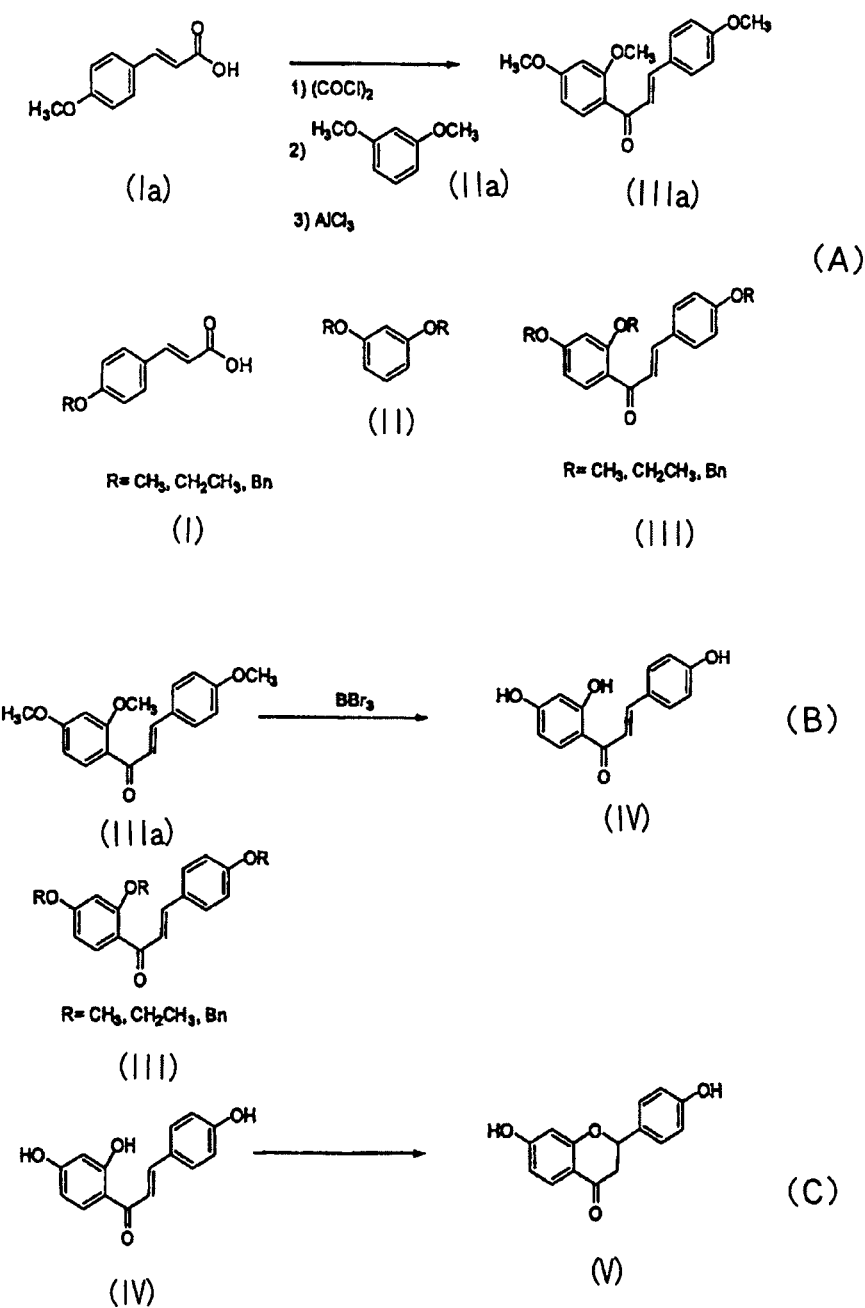
FIG. 1 shows reaction diagrams illustrating the first reaction (A) and the second reaction (B) indicating an example of iso-liquiritigenin according to the present invention.
Figure 2:
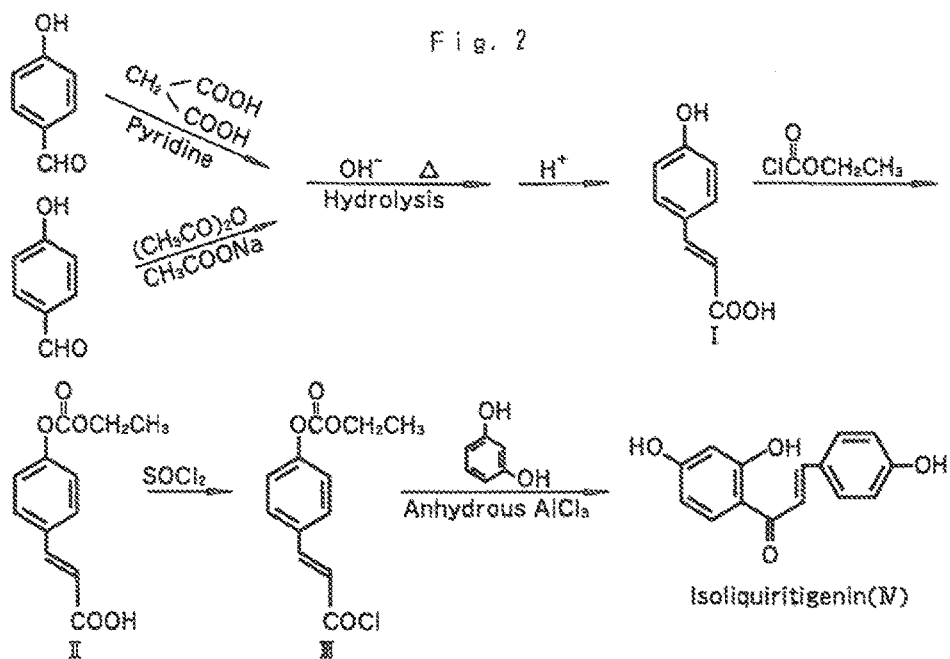
FIG. 2 shows a reaction diagram illustrating an example of producing liquiritigenin by a conventional first method.
Figure 3:
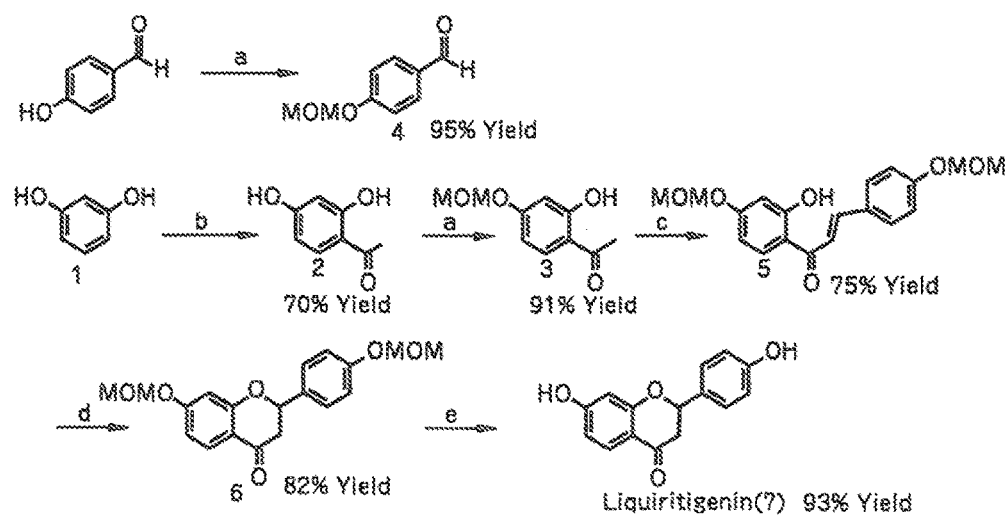
FIG. 3 shows a reaction diagram illustrating an example of producing a liquiritigenin by a conventional second method.

Hereinafter, the present invention will be described with reference to preferred embodiments of the present invention in the Examples.

EXAMPLE 1

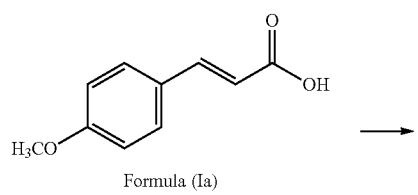

Formula (Ia)

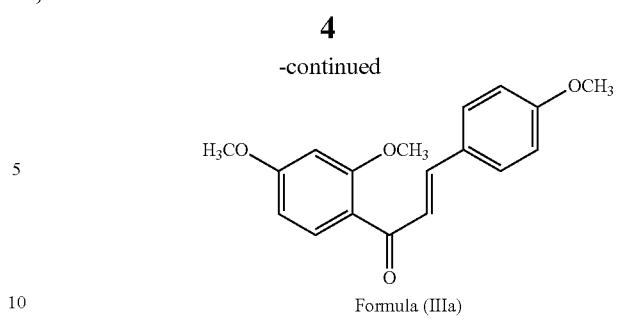

Formula (IIIa)

4-methoxy cinnamic acid (formula (Ia) of 10 g was dissolved in anhydrous methylene chloride of 50 mL with dimethylformamide of 0.25 ml, and then oxalyl chloride of 9.6 mL was added dropwise over 10 minutes at a room temperature, taking care of foaming. After 2 hours of stirring the mixture as it is, at a room temperature, the solvent was removed under a reduced pressure. To the resulting residue, 1,3-dimethoxy-benzene (II a) of 7.4 mL and anhydrous ether of 200 ml were added. In an ice bath, a catalyst anhydrous aluminum trichloride powder of 22.4 g was slowly added to the mixture over a period of 15 minutes. After being left to stand overnight at a room temperature, the content was dropped onto ice (500 g) and 6M hydrochloric acid of 10 mL was added. After the ice dissolved, the mixture was subjected to extraction with ethyl acetate (300 mL) four times. The extract was dried over anhydrous sodium sulfate, and concentrated under a reduced pressure and the residue was crystallized out with ether-hexane mixture to give a crystal product (III a) of 14.2 g. Yield 85% $^1$H-NMR (CDCl$_3$) δ 7.73 (1H, d, J=8.1 Hz), 7.64 (1H, d, J=15.1 Hz), 7.54 (2H, d, J=7.7 Hz), 7.38 (1H, d, J=15.1 Hz), 6.90 (2H, d, J=7.7 Hz), 6.55 (1H, brd, J=8.1 Hz), 6.49 (1H, brs), 3.89 (3H, s), 3.85 (3H, s), 3.83 (3H, s).

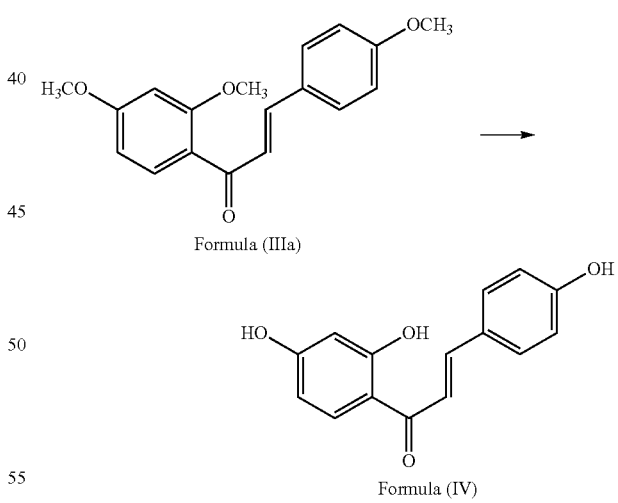

Formula (IIIa)

Formula (IV)

The above product of 3 g was dissolved in methylene chloride of 60 mL and the solution was dropped into 1 M BBr$_3$ methylene chloride solution at 0° C. The mixture was raised to a room temperature and was stirred as it is for two days. The ice-cold water of 700 mL containing a Senietto salt of 34 g and methanol of 350 mL were added thereto, and the mixture was stirred at a room temperature overnight. The resulting yellow solution was extracted twice with ethyl acetate, washed with 1 M Seignette salt (Potassium sodium tartrate)-saturated brine, dried over anhydrous sodium sulfate, and concentrated. The residue was crystallized from ether-hexane, to obtain the desired product (IV) of 1.95 g. The mother liquor again were crystallized with ether-hexane to give the second crystal object of 0.59 g. Total Yield 98%
$^1$H-NMR (acetone-$d_6$) δ 13.5 (1H, s), 8.10 (1H, d, J=8.3 Hz), 7.82 (1H, d, J=15.4 Hz), 7.74 (1H, d, J=15.4 Hz), 7.72 (2H, d, J=8.2 Hz), 6.90 (2H, d, J=8.2 Hz), 6.44 (1H, dd, J=8.3 and 1.7 Hz), 6.34 (1H, d, J=1.7 Hz).

The desired product iso-liquiritigenin were tested for acute toxicity in Japan Food Analysis Center and it was confirmed that there is no toxicity.

EXAMPLE 2

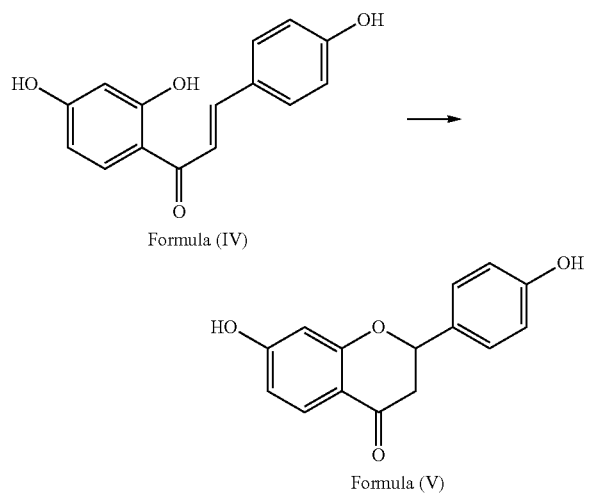

The starting material of 200 mg (Formula IV) was added to a citric acid aqueous solution adjusted at pH 2 to about pH 4, stirred, and after well dispersed, allowed to stand for one day and night at a room temperature. The suspension was concentrated to obtain the crude crystals (Formula V) by crystallization with ether. The analysis values are as follows, It was confirmed that a part of the starting material (Formula IV) was converted to liquiritigenin (–).

1H-NMR (DMSO-$d_6$) δ 9.65 (1H, brs), 7.58 (1H, m), 7.27 (2H, m), 6.74 (2H, m), 6.45 (1H, m), 6.28 (1H, m), 5.39 (1H, brd, J=11.6 Hz), 3.65 (1H, brt, J=15.0 Hz), 2.58 (1H, brd, J=15.7 Hz).

EXAMPLE 3

A soft drink TM "Longevity Challenge" of 50 ml is pH3.9 and mainly composed of Indigestible dextrin, N-acetyl-glucosamine, dextrin, chitin oligosaccharides, chitosan olgosacharldes, lactic acid, and ascorbic acid (vitamin C): soled by International Medical Institute Corporation. So, iso-liquiritigenin of about 100-2000 times of the dose: (effective amount for a mouse) was added to the soft drink as shown in the "suppression action on liquiritigenin of cancer cells." Table 2 described in the patent specification U.S. Pat. No. 5,611,394 to form a supplement for immune enhancement.

According to Table 2 of U.S. Pat. No. 5,611,394, the pharmacological effect at the amount of liquiritigenin (–) of 10 μg/ml, will be predicted as shown in 96.08% against human liver cancer cells SMMC7721, 73.76% against human poorly differentiated gastric cancer line BOC-823, 64.40% against human early young grain cell leukemia cells HL-60, although somewhat less 35.06% against human lung cancer cells A549.

The invention claimed is:
1. A method of preparing iso-liquiritigenin, comprising steps of:
coupling 4-methoxy cinnamic acid represented by formula (Ia) with 1,3-methoxy benzene represented by formula (IIa) through the Friedel-Craft reaction to synthesize tri-methoxy-iso-liquiritigenin represented by formula (IIIa),
crystallizing out the reaction product, and
eliminating the protecting group to obtain iso-liquiritigenin represented by formula (IV)

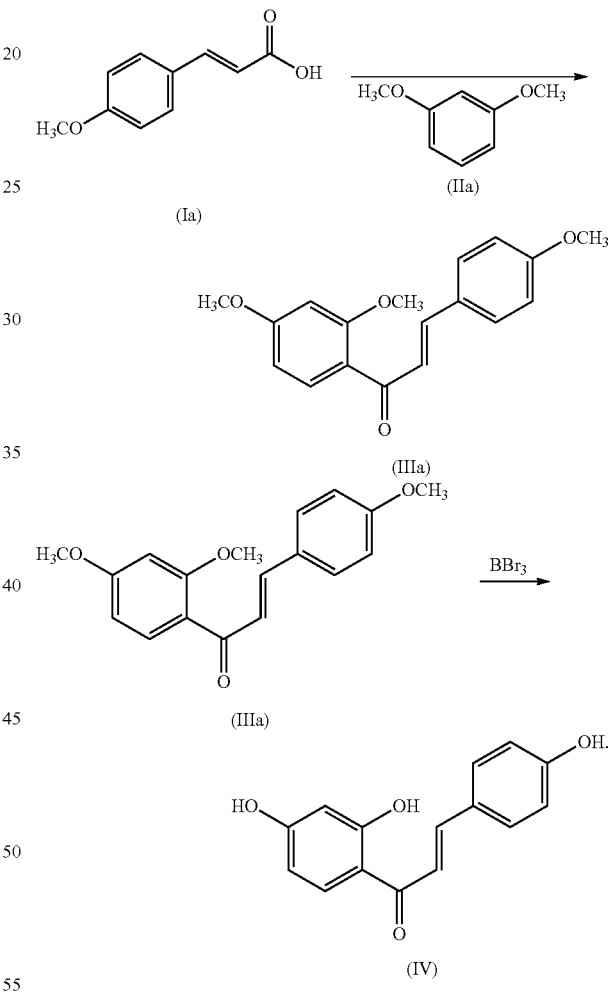

2. The method of preparing iso-liquiritigenin according to claim 1, wherein the Friedel-Craft reaction is carried out by steps of:
dissolving 4-methoxy cinnamic acid represented by formula (Ia) in anhydrous methylene chloride with dimethylformamide;
adding oxalyl chloride $(COCl)_2$;
removing the solvent under a reduced pressure to get a resulting residue;
adding 1,3-methoxy benzene represented by formula (IIa) and anhydrous ether to get the mixture;

adding a catalyst anhydrous aluminum trichloride (AlCl$_3$) to the mixture, and synthesizing tri-methoxy-iso-liquiritigenin represented by formula (IIIa).

\* \* \* \* \*